United States Patent [19]

Kobayashi et al.

[11] Patent Number: 5,510,533

[45] Date of Patent: Apr. 23, 1996

[54] PROCESS FOR PRODUCING 3,5-DIFLUOROANILINE AND DERIVATIVE THEREOF

[75] Inventors: Hiroshi Kobayashi, Fukuoka; Masaaki Shimizu, Tokyo; Haruaki Ito, Kanagawa, all of Japan

[73] Assignee: SDS Biotech K. K., Tokyo, Japan

[21] Appl. No.: 710,475

[22] Filed: Jun. 5, 1991

[30] Foreign Application Priority Data

| Jun. 6, 1990 | [JP] | Japan | 2-146219 |
| Jun. 22, 1990 | [JP] | Japan | 2-162827 |
| Jul. 4, 1990 | [JP] | Japan | 2-175260 |

[51] Int. Cl.$^6$ ............................................. C07C 209/10
[52] U.S. Cl. ............................ 564/407; 564/405; 570/143
[58] Field of Search ........................... 564/407, 405

[56] References Cited

U.S. PATENT DOCUMENTS 3,663,620  5/1972  Merianos et al. ................... 564/407

FOREIGN PATENT DOCUMENTS 2389596  1/1978  France .
1079176  8/1967  United Kingdom ............... 564/407

OTHER PUBLICATIONS

Sokolenko et al. *Chem. Abs.* 74(13) 63996c (1971).
G. Schimemann et al, "Chimen und Technologie cyclischer Fluorverbindungen", 1969, pp. 50–53, Ferdinand Enke Verlag, Stuttgart, DE.

Chemical Abstracts, vol. 65, 1966, Abstract No. 13581c, Columbus, Ohio, US; N. Ishikawa: "3–5 Diflouoraniline & 5–fluoro–1,3–penylendediamine", & Nippon Kagaku Zasshi 86(11), 1202–3 (1965).

Journal of Fluorine Chemistry, Vo. 1, No. 4, Apr. 1972, pp. 415–425; G. C. Finger et al.: "Flourination of 1,2,3,4– and 1,2,3,5–tetrahalobenzenes with potassium fluoride in dimethyl sulfone".

Journal of The Chemistry Society Perkin II, 1974, pp. 76–79; S. I. Ette et al.: "The Kinetics of the reactions of picryl chloride with some substituted anilies. Part II".

Nihon Kagaku Zasshi, vol. 87, 1966, p. 1089.

Journal of American Chemistry Society, vol. 81, 1959, pp. 94–101.

Journal of American Chemistry Society, vol. 73, 1951, pp. 153–155.

*Primary Examiner*—Brian M. Burn
*Attorney, Agent, or Firm*—Sughrue, Mion, Zinn, Macpeak & Seas

[57] ABSTRACT

A process for production of a 3,5-difluoroaniline compound with ease is disclosed, which comprise reacting an aminating agent with a 1,3,5-trifluorobenzene compound.

10 Claims, No Drawings

PROCESS FOR PRODUCING 3,5-DIFLUOROANILINE AND DERIVATIVE THEREOF

FIELD OF THE INVENTION

The present invention relates to a process for producing 3,5-difluoroaniline and a derivative thereof which are useful, for example, as an intermediate product for pharmaceuticals.

BACKGROUND OF THE INVENTION

For preparation of 3,5-difluoroaniline there have been known the method described in Finger et al, *J. Am. Chem. Soc.*, 73, 153 (1951), wherein 3,5-difluoroaniline is prepared from 2,4-difluoroaniline as a starting material through five reaction steps; and Ishikawa et al, *Nihon Kagaku Zasshi*, 87, 1089 (1966) and ibid 86, 1202 (1965), wherein 1,3,5-trichloro-2,4,6-trifluorobenzene is used as a starting material.

The former method, however, involves many reaction steps for synthesis of the starting material 2,4-difluoroaniline, and produce the final product only in a low yield. 1,3,5-Trichloro-2,4,6-trifluorobenzene used in the latter method as a starting material is prepared from hexachlorobenzene, which has been designated as a specific chemical substance of the first type under "Law Concerning the Examination and Regulation of Manufacture, Etc. of Chemical Substances" in Japan, so that hexachlorobenzene is not readily available and handling of the compound involves various problems.

2-Chloro-3,5-difluoroaniline has been known to be produced by substituting an amino group of 2,4-difluoro- 6-nitroaniline with a chlorine atom and then converting the nitro group into an amino group, as described in Finger et al, *J. Fluorine Chem.*, 1, 415–425 (1971/1972). In more detail, the process comprises subjecting 2,4-difluoroaniline to acetylation and nitration (according to the method as described in Finger et al, *J. Amer. Chem. Soc.*, 73, 153 (1951)) to synthesize 2,4-difluoro-6-nitroaniline, followed by diazotization of the amino group of the compound in the presence of cuprous chloride (Sandmeyer reaction), and then reducing the resulting 2-chloro-3,5-difluoronitrobenzene to obtain 2-chloro-3,5-difluoroaniline. This process involves many reaction steps and provides the final product only in a low yield.

SUMMARY OF THE INVENTION

An object of the present invention is to provide a process for producing 3,5-difluoroaniline and a derivative thereof, which is free from the problems encountered in the prior art methods.

That is, the present invention is a process for producing a 3,5-difluoroaniline compound represented by formula (I)

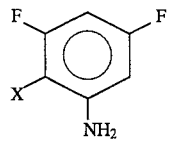

which comprises reacting an aminating agent with a 1,3,5-trifluorobenzene compound represented by formula (II)

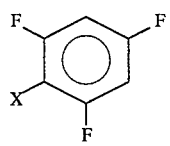

wherein X is a hydrogen atom or a chlorine atom.

DETAILED DESCRIPTION OF THE INVENTION

The 1,3,5-trifluorobenzene compound of formula (II) can be obtained by decarboxylation of a 2,4,6-trifluoroisophthalic acid compound represented by formula (III)

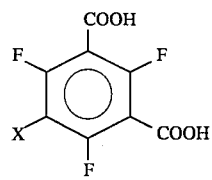

wherein X is the same as defined above.

Conventional decarboxylation reactions can be applied in the present invention, but the decarboxylation reaction is preferably conducted by heating the compound of formula (III) in a polar solvent with or without an alkali.

Water or an aprotic polar solvent is preferably used as a solvent for the decarboxylation reaction. Examples of the aprotic polar solvent include dimethyl sulfoxide, dimethylformamide, dimethylacetamide, N-methyl- 2-pyrrolidone, benzonitrile, quinoline, pyridine, sulfolane and hexamethylphosphoramide. The solvent is used preferably in an amount (by weight) 1 to 100 times that of the 2,4,6-trifluoroisophthalic acid compound.

Examples of alkalis used include sodium hydrogencarbonate, potassium hydrogencarbonate, sodium carbonate and potassium carbonate, and it can be used in an amount of 0.01 to 10 mols, preferably 0.05 to 1 mol, per mol of the 2,4,6-trifluoroisophthalic acid compound.

The reaction temperature varies depending on the type of the reaction solvent, and it is generally 110° to 350° C., preferably 120° to 180° C.

The reaction terminates when generation of gaseous carbon dioxide ceases, and the reaction time is generally 0.1 to 10 hours, preferably 0.3 to 8 hours.

The objective compound of formula (II) can be isolated by removing the reaction solvent, and distilling the reaction mixture.

Further, dechlorination reaction of 2-chloro- 1,3,5-trifluorobenzene which is one compound of formula (II) can provide 1,3,5-trifluorobenzene which is the other compound of formula (II). The dechlorination reaction is preferably conducted by heating 2-chloro- 1,3,5-trifluorobenzene in the presence of metal and water under applied pressure.

This reaction is a high temperature reaction, and accordingly it is carried out in an autoclave. Examples of the metal used include copper powder, Raney alloy and zinc-copper couple as prepared by adding an aqueous solution of copper sulfate to an aqueous dispersion of zinc powder, and those having a large surface area are preferred. Of these metals, copper powder and zinc-copper couple are preferred, and they are preferably used in an amount of 1.0 to 10.0 g atom, more preferably 1.2 to 3.5 g atom, as copper or zinc-copper per mol of 2-chloro-1,3,5-trifluorobenzene. Water is used in an amount (by mol) 0.5 to 2.0 times that of 2-chloro-1,3,5-trifluorobenzene. The reaction temperature is preferably 200° to 400° C. and more preferably 300° to 400° C. The reaction time is 1 to 48 hours, though it varies depending upon the reaction temperature and stirring efficiency. After completion of the reaction, 1,3,5-trifluorobenzene can be isolated by distilling off the reaction mixture under normal pressure.

1,3,5-trifluorobenzene can also be obtained by the known method as described in *J. Amer. Chem. Soc.*, 73, 153 (1951).

5-Chloro-2,4,6-trifluoroisophthalic acid, one compound of formula (III) used as a starting material in the above-described decarboxylation reaction can be prepared from tetrachloroisophthalonitrile which is an effective component of Daconil (trade name, an agricultural and horticultural fungicide) by the method described in *Kogyo Kagaku Zasshi*, 73, 447 (1970). Further, 2,4,6-trifluoroisophthalic acid, the other compound of formula (III), can be obtained by dechlorination of 5-chloro-2,4,6-trifluoroisophthalic acid, according to the method described in *Kogyo Kagaku Zasshi*, 73, 972 (1970). Thus, these compounds are easily available, and can be handled easily.

In the process of the present invention, one fluorine atom of the 1,3,5-trifluorobenzene compound of formula (II) is substituted With an amino group to form the 3,5-difluoroaniline compound of formula (I). The substitution reaction is preferably carried out by reacting the 1,3,5-trifluorobenzene compound and an aminating agent in a polar solvent with heating.

Examples of the aminating agent include ammonia, aqueous ammonia, and metal amide salts such as sodium amide, potassium amide and lithium amide. Of these, ammonia is particularly preferred. The aminating agent is used in an amount (by mol) 1 to 100 times that of the 1,3,5-trifluorobenzene compound though the amount varies depending on the type of the agents.

Polar solvents capable of dissolving the aminating agent are preferred as a reaction solvent. Among them, acetonitrile, methanol and ethanol are particularly preferred in view of easy isolation of the product.

The reaction temperature is preferably 100° to 300° C. and more preferably 150° to 300° C. The reaction time is preferably 2 to 120 hours, more preferably 2 to 96 hours when an autoclave is used as the reaction vessel, though the time depends on the type of the aminating agent. The final product is isolated preferably by steam distillation after the reaction.

One preferred embodiment of the present invention is a process comprising the steps of (i) decarboxylating 5-chloro-2,4,6-trifluoroisophthalic acid to form 2-chloro-1,3,5-trifluorobenzene, (ii) dechlorinating the 2-chloro-1,3,5-trifluorobenzene to form 1,3,5-trifluorobenzene, and then (iii) substituting an amino group for one fluorine atom of the 1,3,5-trifluorobenzene to form 3,5-difluoroaniline.

In the case, the process of the present invention provides 3,5-difluoroaniline from 5-chloro- 2,4,6-trifluoroisophthalic acid only through the three reaction steps.

In the above process, the product of the reaction step (i) and that of the reaction step (ii) can be used for the subsequent reaction step, respectively, without isolation and purification, but they are preferably used after isolation and purification.

The 3,5-difluoroaniline compound of formula (I) is very useful as an intermediate product for pharmaceuticals, agricultural chemicals or industrial chemicals as described in, for example, *J. Amer. Chem. Soc.*, 81, 94–101 (1959).

The present invention is further explained with reference to the following Examples, but the invention should not be construed as being limited thereto.

EXAMPLE 1

(Preparation of 2-chloro-1,3,5-trifluorobenzene)

60 g of 5-chloro-2,4,6-trifluoroisophthalic acid was added to 90 ml of N,N-dimethylformamide, and the mixture was heated with stirring on an oil bath at 150° C. Carbon dioxide began to evolve at first, and then 2-chloro-1,3,5-trifluorobenzene was distilled off. The distillate was cooled and collected with a Liebig condenser. The generation of carbon dioxide ceased after heating the mixture for about 1 hour, and the mixture was further heated until the distillation of the oily component ceased. The distillate was washed with water, and the oil layer was dried over sodium sulfate to obtain a crude product of 2-chloro-1,3,5-trifluorobenzene in an amount of 36.1 g (yield 92%).

The results of NMR analysis of the crude product are as follows:

$^1$H NMR (CDCl$_3$/TMS): 6.75 ppm $^{19}$F NMR (CDCl$_3$/C$_6$F$_6$): 51.98 ppm (m,2F), 52.66 ppm (m,1F)

A part of the crude product was rectified to obtain a fraction having a boiling point of 121° to 123° C. (reported b.p.: 124° C.).

EXAMPLE 2

(Preparation of 1,3,5-trifluorobenzene)

An autoclave was charged with 66.8 g of 2-chloro-1,3,5-trifluorobenzene, 5 g of water and 65 g of copper powder, and the content was heated at 300° C. with high speed stirring for 28 hours. After the reaction, the content was distilled off, and the fraction distilled at 74° to 77° C. was collected and dried over sodium sulfate to obtain 1,3,5-trifluorobenzene in an amount of 38.5 g (yield 73%).

The results of NMR analysis of the compound are as follows:

$^1$H NMR (CDCl$_3$/TMS): 6.61 ppm $^{19}$F NMR (CDCl$_3$/C$_6$F$_6$): 54.6 ppm (m)

EXAMPLE 3

(Preparation of 1,3,5-trifluorobenzene)

An autoclave was charged with 6.68 g of 2-chloro-1,3,5-trifluorobenzene, 0.5 g of water and 7.5 g of 3–5% zinc-copper couple (prepared by adding an aqueous solution of copper sulfate to an aqueous dispersion of zinc powder (copper/zinc weight ratio of 3 to 5%), allowing the mixture to stand, filtering out the solid component under reduced pressure, and washing, drying and pulverizing the solid component in a mortar), and the content was heated at 330° C. with high speed stirring for 32 hours. After the reaction, the content was distilled off, and a fraction distilled off at 74° to 77° C. was dried over sodium sulfate to obtain 1,3,5-trifluorobenzene in an amount of 2.19 g (yield 42%).

EXAMPLE 4

(Preparation of 1,3,5-trifluorobenzene)

44 g of 2,4,6-trifluoroisophthalic acid and 11 g of potassium carbonate were added to 90 ml of N,N-dimethylformamide, and the mixture was heated with stirring on an oil bath at 150° C. Carbon dioxide began to evolve at first, and then 1,3,5-trifluorobenzene was distilled off. The distillate was cooled and collected with a Liebig condenser. The generation of carbon dioxide ceased after heating the mixture for about 3 hours, and the mixture was further heated until the distillation of the oily component ceased. The distillate was washed with water, and the oil layer was dried over sodium sulfate to obtain a crude product of 1,3,5-trifluorobenzene in an amount of 23.3 g (yield 88%).

The results of NMR analysis of the crude product are as follows:

$^1$H NMR (CDCl$_3$/TMS): 6.61 ppm $^{19}$F NMR (CDCl$_3$/C$_6$F$_6$): 54.6 ppm (m)

A part of the crude product was rectified to obtain a fraction having a boiling point of 74° to 76° C. (reported b.p.: 75.5° C.).

EXAMPLE 5

(Preparation of 1,3,5-trifluorobenzene)

22 g of 2,4,6-trifluoroisophthalic acid was added to 80 ml of sulfolane, and the mixture was heated with stirring on an oil bath at 200° C. Subsequently, the same procedure as in Example 4 was repeated, whereby 11 g (yield 83%) of a crude product of 1,3,5-trifluorobenzene was obtained.

EXAMPLE 6

(Preparation of 3,5-difluoroaniline)

26.5 g of 1,3,5-trifluorobenzene and 200 ml of methanol saturated with ammonia gas at room temperature were sealed in a Teflon-coating autoclave and heated on an oil bath at 200° C. for 60 hours. After the reaction, the solvent and unreacted 1,3,5-trifluorobenzene were distilled off from the reaction mixture under reduced pressure, and the remaining mixture of a solid component and an oily component was extracted with ether to obtain an oily product in an amount of 24.8 g (yield of 3,5-diftuoroaniline: 93% determined by GLC analysis).

The results of NMR analysis of the oily product are as follows:

$^1$H NMR (CDCl$_3$/TMS): 4.16 ppm (br,2H), 6.01 ppm (m,1H), 6.27 ppm (m,2H)

$^{19}$F NMR (CDCl$_3$/C$_6$F$_6$): 51.07 ppm, 51.14 ppm

Furthermore, the oily product was rectified to obtain 3,5-difluoroaniline having a boiling point of 80° C./20 mmHg and a melting point of 39° to 40° C.

EXAMPLE 7

(Preparation of 3,5-difluoroaniline)

The procedure of Example 6 was repeated except that 9.6 g of sodium amide was used in place of ammonia, and acetonitrile was used in place of methanol. GLC analysis confirmed that 3,5-difluoroaniline was obtained in a yield of 51%.

EXAMPLE 8

(Preparation of 2-chloro-3,5-difluoroaniline)

33.4 g of 2-chloro-1,3,5-trifluorobenzene and 200 ml of methanol saturated with ammonia gas at room temperature were sealed in a Teflon-coating autoclave and heated on an oil bath at 160° C. for 40 hours. After the reaction, the solvent and unreacted 2-chloro-1,3,5-trifluorobenzene were distilled off from the reaction mixture under reduced pressure, and the remaining mixture of a solid component and an oily component was extracted with ether to obtain an oily product in an amount of 31.7 g (yield of 2-chloro-3,5-difluoroaniline: 95% determined by GLC analysis).

The results of IR and NMR analysis of the oily product are as follows:

IR (film): 3500, 3400, 1635, 1585, 1490, 1450, 1370, 1300, 1205, 1120, 1070, 1035, 990, 820, 795 cm$^{-1}$ $^1$H NMR (CDCl$_3$/TMS): 4.28 ppm (br,2H), 6.20 ppm (m,1H), 6.24 ppm (m,1H)

$^{19}$F NMR (CDCl$_3$/C$_6$F$_6$): 49.55 ppm (q,1F), 50.26 ppm (t,1F)

When proton-decoupling done: 49.55 ppm (d), 50.27 ppm (d) J=7.32 Hz

An acetylated compound of the oily product had a melting point of 89° to 90° C. (reported m.p.: 86.5°–87° C.).

EXAMPLE 9

(Preparation of 2-chloro-3,5-difluoroaniline)

The procedure of Example 8 was repeated except that the temperature of the oil bath was changed to 180° C. and the reaction was conducted for 28 hours. GLC analysis confirmed that 2-chloro-3,5-difluoroaniline was obtained in a yield of 93%.

EXAMPLE 10

(Preparation of 2-chloro-3,5-difluoroaniline)

The procedure of Example 8 was repeated except that 9.6 g of sodium amide was used in place of ammonia, and acetonitrile was used in place of methanol. GLC analysis confirmed that 2-chloro-3,5-difluoroaniline was obtained in a yield of 79%.

While the invention has been described in detail and with reference to specific embodiments thereof, it will be apparent to one skilled in the art that various changes and modifications can be made therein without departing from the spirit and scope thereof.

What is claimed is:

1. A process for producing a 3,5-difluoroaniline compound represented by formula (I)

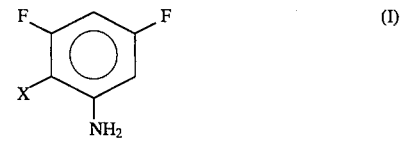

comprising the steps of:

(a) decarboxylating a 2,4,6-trifluoroisophthalic acid compound of formula (III)

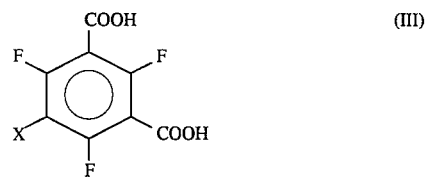

to thereby obtain the 1,3,5-trifluorobenzene compound represented by formula (II)

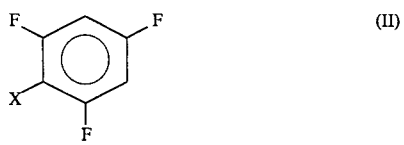

and (b) reacting an aminating agent with said 1,3,5-trifluorobenzene compound represented by formula (II) to produce said 3,5-difluoroaniline compound represented by formula (I);

wherein X represents a hydrogen atom or a chlorine atom.

2. A process for producing a 3,5-difluoroaniline compound represented by formula (I)

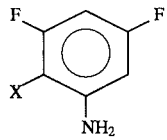

wherein X represents a hydrogen atom, comprising the steps of:

(a) decarboxylating a 2,4,6-trifluoroisophthalic acid compound of formula (III)

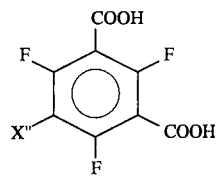

wherein X" represents a chlorine, to thereby obtain 2-chloro-1,3,5-tri-fluorobenzene;

(b) dechlorinating said 2-chloro-1,3,5-tri-fluorobenzene to thereby obtain the 1,3,5-trifluorobenzene compound represented by formula (II)

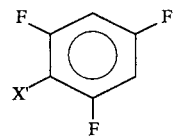

wherein X' represents a hydrogen atom; and (c) reacting an aminating agent with said 1,3,5-trifluorobenzene compound represented by formula (II) to produce said 3,5-difluoroaniline compound represented by formula (I).

3. The process as in claim 1, wherein the reaction with the aminating agent is carried out in a polar solvent with heating.

4. The process as an claim 1, wherein the aminating agent is ammonia, aqueous ammonia or a metal amide salt.

5. The process as in claim 3, wherein the aminating agent is ammonia, aqueous ammonia or a metal amide salt.

6. The process as claim 4, wherein the aminating agent is ammonia.

7. The process as in claim 5, wherein the aminating agent is ammonia.

8. The process as in claim 1, wherein the decarboxylation reaction is carried out in water or an aprotic polar solvent with heating.

9. The process as in claim 2, wherein the dechlorination reaction is carried out by heating 2-chloro- 1,3,5-trifluorobenzene in the presence of metal and water under applied pressure.

10. The process as in claim 8, wherein the decarboxylation reaction is conducted in the presence of an alkali.

* * * * *